United States Patent
Harrison et al.

(10) Patent No.: US 9,249,661 B2
(45) Date of Patent: Feb. 2, 2016

(54) APPARATUS AND METHODS FOR DETERMINING COMMINGLING COMPATIBILITY OF FLUIDS FROM DIFFERENT FORMATION ZONES

(75) Inventors: Christopher Harrison, Auburndale, MA (US); Farshid Mostowfi, Edmonton (CA); Matthew T. Sullivan, Westwood, MA (US); Elizabeth Smythe, Cambridge, MA (US); Abdel M. Kharrat, Edmonton (CA)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 585 days.

(21) Appl. No.: 13/355,049

(22) Filed: Jan. 20, 2012

(65) Prior Publication Data

US 2013/0188169 A1 Jul. 25, 2013

(51) Int. Cl.
 E21B 49/08 (2006.01)
 G01N 33/28 (2006.01)
 G01N 21/85 (2006.01)
 G01N 21/25 (2006.01)
 G01N 21/59 (2006.01)
 G01N 21/64 (2006.01)

(52) U.S. Cl.
 CPC .......... *E21B 49/088* (2013.01); *G01N 21/5907* (2013.01); *G01N 21/85* (2013.01); *G01N 33/2823* (2013.01); *G01N 21/25* (2013.01); *G01N 21/64* (2013.01); *G01N 2021/8571* (2013.01)

(58) Field of Classification Search
 None
 See application file for complete search history.

(56) References Cited

U.S. PATENT DOCUMENTS

| | | | |
|---|---|---|---|
| 3,582,284 A * | 6/1971 | Hamshere et al. | 422/535 |
| 4,436,635 A * | 3/1984 | Abrams et al. | 210/806 |
| 6,401,547 B1 | 6/2002 | Hatfield et al. | |
| 7,243,720 B2 | 7/2007 | Ligtemlm | |
| 7,575,681 B2 | 8/2009 | Angelescu et al. | |
| 7,695,629 B2 | 4/2010 | Salamitou et al. | |
| 7,799,278 B2 | 9/2010 | Salamitou et al. | |
| 7,855,169 B2 | 12/2010 | Pope et al. | |
| 2003/0080061 A1 * | 5/2003 | Underdown et al. | 210/650 |
| 2008/0066537 A1 | 3/2008 | Hegeman et al. | |
| 2010/0012586 A1 | 1/2010 | Angelescu et al. | |
| 2010/0229623 A1 | 9/2010 | Abad et al. | |
| 2010/0265492 A1 | 10/2010 | Schroeder et al. | |
| 2011/0172924 A1 * | 7/2011 | Hughes et al. | 702/11 |
| 2011/0292382 A1 | 12/2011 | Mostowfi et al. | |

FOREIGN PATENT DOCUMENTS

JP 2003513263 4/2003

OTHER PUBLICATIONS

International Search Report and Written Opinion of PCT Application No. PCT/US2013/020627 dated Apr. 8, 2013: pp. 1-9.

* cited by examiner

*Primary Examiner* — Gordon J Stock, Jr.
(74) *Attorney, Agent, or Firm* — Daniel S. Matthews

(57) ABSTRACT

An apparatus and a method including exposing a first fluid to a pre-filter, observing the first fluid, introducing a second fluid to the first fluid, exposing the first and second fluids to a filter, and observing the first and second fluids wherein the observing the first fluid and observing the first and second fluids comprise optical measurements and the first fluid comprises material from a subterranean formation. Some embodiments may compare the optical measurements of the first fluid and the first and second fluids and/or estimate the first fluid's likelihood of forming precipitants with other fluids and/or the first fluid's asphaltene content.

18 Claims, 10 Drawing Sheets

APPARATUS AND METHODS FOR DETERMINING COMMINGLING COMPATIBILITY OF FLUIDS FROM DIFFERENT FORMATION ZONES

BACKGROUND

Oil wells may include multiple hydrocarbon zones (e.g., payzones, hydrocarbon zones, formation zones) that are fluidically and/or hydraulically isolated. In production, some oilfield operators prefer to use a single installation of production tubing to produce fluids from all of the zones. During the production process, using a single installation of production tubing mixes the fluids from the different payzones. However, fluids from the different zones may or may not be compatible.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Embodiments relate to an apparatus and a method including exposing a first fluid to a pre-filter, observing the first fluid, introducing a second fluid to the first fluid, exposing the first and second fluids to a filter, and observing the first and second fluids wherein the observing the first fluid and observing the first and second fluids comprise optical measurements and the first fluid comprises material from a subterranean formation. Some embodiments may compare the optical measurements of the first fluid and the first and second fluids and/or estimate the first fluid's likelihood of forming precipitants with other fluids and/or the first fluid's asphaltene content. Embodiments relate to an apparatus and method for characterizing a fluid property including a pre-filter in communication with a fluid from a formation, an optical sensor to observe the fluid from the pre-filter, a fluid combination device in communication with the fluid and a second fluid source, a filter in communication with the combination device, a second optical sensor to observe a third fluid from the filter, and a processor to compare data collected by the sensor and second sensor.

FIGURES

Embodiments of systems and methods of determining parameter values in a downhole environment are described with reference to the following figures. The same numbers are used throughout the figures to reference like features and components.

DETAILED DESCRIPTION

Figure 1:
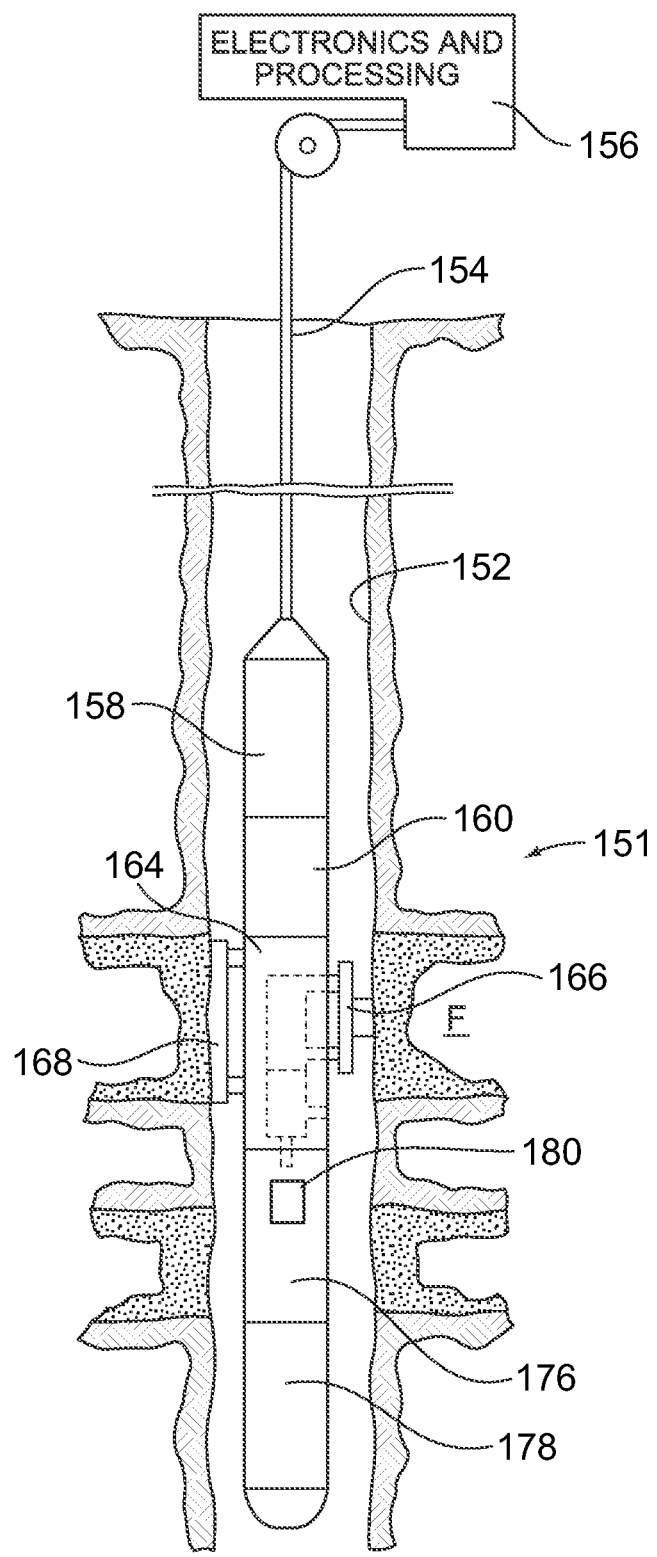
FIG. 1 illustrates an example system in which embodiments of the systems and methods for determining commingling compatibility of fluids from different formation zones can be implemented.

In the following detailed description of the preferred embodiments, reference is made to the accompanying drawings, which form a part hereof, and within which are shown by way of illustration specific embodiments by which the examples described herein may be practiced. It is to be understood that other embodiments may be utilized and structural changes may be made without departing from the scope of the disclosure.

The examples disclosed herein relate to downhole methods and systems that enable the determination of asphaltene content of a fluid sample(s) downhole and/or whether live crude oils from different production zones can be commingled during oil well production. More generally, the examples disclosed herein determine downhole the stability of mixing crude oils in an open hole and/or cased hole sampling operation. The methods and systems disclosed herein may be implemented in downhole tools and/or wireline-conveyed tools such as the MDT Modular Formation Dynamics Tester (which is commercially available from the Schlumberger Technology Corporation of Sugar Land, Tex.).

The examples disclosed herein may be used to determine a characteristic of a fluid sample (e.g., crude oil) downhole by mixing it with another substance. The characteristic may be an amount of asphaltenes of the fluid sample and the other substance may be heptane, pentane, etc. The fluid sample may be obtained from the adjacent borehole and stored (e.g., temporarily stored) in a sample chamber at a given temperature and/or pressure. The temperature at which the sample is stored may be the temperature of the borehole and/or a temperature that is higher than the borehole temperature due to electronics of the downhole tool.

To determine a first optical density value(s) of the fluid sample, a portion of the fluid sample is pumped through a flowline and past one or more optical sensors. The optical sensors or detectors may obtain optical density values of the fluid samples at a series of pre-defined wavelengths. The optical path may be relatively short to ensure that the fluid sample does not appear opaque to the optical sensors. The portion of the fluid sample from which the first optical density values(s) is obtained may then be pumped through the example apparatus and out to the borehole.

To cause asphaltenes to precipitate from the rest of the fluid sample (e.g., maltenes), heptane stored in a chamber of the downhole tool is brought to a substantially identical pressure as the fluid sample and then simultaneously pumped into a flowline into which the fluid sample is also being pumped. The heptane may be pumped into the flowline at a first flowrate and the fluid sample may be pumped into the flowline at a second flowrate such that a mixing ratio of the fluids is obtained and/or achieved (e.g., 40:1 mixing ratio). Prior to its usage, the heptane may be stored in a separate chamber that is filled prior to the downhole tool being deployed downhole.

To efficiently mix the heptane and the fluid sample, the mixed fluids may be directed through a passive mixer. The passive mixer may include a torturous flowpath that maximizes the mixing efficiency between the heptane and the fluid sample (e.g., the crude oil). To filter any asphaltenes that may have flocculated from the mixture, the mixed fluids are directed through a filter and/or membrane that has sufficiently small pores (e.g., 0.435 microns) to substantially prevent the passage of flocculated asphaltenes, but enables the remainder of the mixed fluids to pass therethrough.

After passing through the filter, a second optical density value of the mixed fluids may be obtained. To determine an amount of asphaltenes flocculated from the fluid sample, the first optical density value may be compared to the second optical density value. If the first and second optical density values are substantially the same, no significant flocculation of asphaltenes took place. However, if there is a difference between the first and second optical densities values, at least some light-absorbing or light-scattering asphaltenes were filtered out by the filter. To determine an amount of asphaltenes contained in the live fluid sample, a difference between the first and second optical density values may be interpreted using methods described in U.S. patent application Ser. No. 12/790,927, filed May 31, 2010, which is hereby incorporated herein by reference in its entirety.

In some examples, asphaltenes filtered out by the filter may be removed by flushing the filter, flowline(s) and/or system with toluene or other solvent (e.g., a similar solvent). The toluene may be pumped through the example apparatus and out to the borehole after flushing the filter, flowline(s) and/or system. Prior to its usage, the toluene may be stored in a separate chamber that is filled prior to the downhole tool being deployed downhole.

To determine whether or not two or more fluid samples (e.g., crude oils) can be commingled without significant asphaltene flocculation, the fluid samples may be mixed and filtered in a manner as described above. The fluid samples may be mixed at any desired mixing ratio such as 1:1; 4:1, etc. In some examples, the mixing ratio selected corresponds to the production rate of first and second production zones from which the corresponding first and second fluid samples are obtained. For example, the fluid samples may be mixed at a ratio of 4:1 if the crude oil from a first production zone is to be produced at an anticipated rate of 4 times higher than crude oil from a second production zone. Flowing the fluid samples at different flow rates may be beneficial when asphaltenes have different extinction coefficients.

The examples disclosed herein may obtain and store live fluid samples that are from different production zones and which are to be analyzed and/or tested downhole. In some examples, a plurality of first sample chambers (e.g., six chambers) into which fluid samples are to be stored may be selectively coupled to a first pump (e.g., a micropiston) and a plurality of second sample chambers (e.g., six chambers) into which fluid samples are to be stored may be selectively coupled to a second pump (e.g., a micropiston). The fluid sample(s) may flow and/or be pumped through a membrane that substantially removes water and/or particulate from the fluid(s) to be stored in a respective sample chamber (e.g., the piston bore). The examples disclosed herein enable stored fluid samples (e.g., samples having high asphaltene content) to remain stable with respect to temperature variations when moving the tool to different formation zones by enabling the fluid samples to be stored at or above a particular pressure (e.g., above reservoir pressure, an overpressure, a pressure that increases with depth and/or temperature, etc.).

Prior to mixing the samples, a sensor(s) and/or an optical cell(s) (e.g., a microfluidic optical sensor) may independently determine a first optical density value at a predetermined wavelength for a portion of a first downhole fluid sample and a second optical density value at a predetermined wavelength for a portion of a second downhole fluid sample. The fluid samples may be mixed by independently pumping the fluid samples from the respective sample chambers at a controlled flow rate(s) (e.g., substantially equal volumetric flow rates) toward, for example, a flowline having a mixer and/or a filter. While two fluid samples are described as being mixed, any other number (e.g., 3, 4, etc.) of fluid samples may be mixed instead. The mixer may be an active, static and/or passive mixer that includes a torturous flowpath that accelerates the rate at which the fluid samples mix. The filter may be a dead-end filter that substantially blocks the passage of flocculated asphaltenes. In some examples, the filter is a cross flow filter that is positioned sideways (e.g., at a non-perpendicular position relative to a longitudinal axis of the flowline) within the flowline.

In some embodiments, the cross-flow filter wicks fluid slowly from the main tool flowline and conveys the filtered fluid to the microfluidic capillary flowlines. The filters that are in the small microfluidic lines need to be dead-end filters, where the fluid flow is perpendicular to the membrane surface and all fluid goes through the membrane (but not particulates).

In some examples, to simulate the mixed fluids flowing through production tubing to the surface, the pressure of the fluid samples may be decreased from the storage pressure prior to mixing and/or the temperature of the flowline through which the fluid samples are to flow may be decreased prior to mixing the fluid samples using, for example, a Peltier cooler. While the above example describes mixing different fluid samples, in other examples, to determine an amount of asphaltenes present in a fluid sample (e.g., a first fluid sample), the fluid sample may be mixed with a substance (e.g., heptane) and thereafter analyzed. The heptane may be mixed with the crude oil sample at a 40:1 mixing ratio.

To determine if and/or an amount of asphaltenes that may have flocculated when mixing the fluid samples, a sensor(s) and/or an optical cell(s) (e.g., a microfluidic optical sensor) may determine a third optical density value at a predetermined wavelength for the mixed fluid samples. The first and second optical density values may be averaged to generate an averaged optical density value and the averaged optical density value may be compared to the third optical density value. In some examples, a difference between the third optical density value and the averaged optical density value corresponds to the optical spectrum of the asphaltenes in the mixed fluid samples. The asphaltene content of the fluid samples can be determined using a calibration curve, the optical density difference and/or a coefficient of determination ($R^2$). If the third optical density value is less than the averaged optical density value, asphaltenes have flocculated from the mixed fluid samples and have been filtered out of the mixed fluid samples by the filter. If the third optical density value is substantially similar to the averaged optical density value, substantially no asphaltenes have flocculated from the mixed fluid samples. In some examples, after the commingling analysis is complete, toluene is pumped through the filter to substantially remove any asphaltenes that may be trapped therein.

To probe and/or determine the kinetics of the asphaltene flocculation process, an amount of time between mixing the fluid samples and the time of measurement (e.g., when the optical density value of the sample(s) is determined) may be varied. The kinetics of the asphaltene flocculation process may be used to determine and/or provide an indicator of the stability of the commingled solution. In some examples, the kinetics of the asphaltene flocculation process can be probed and/or determined by varying the flow rate of the fluid samples.

For example, to determine the commingling compatibility of two fluid samples at a mixing ratio of 1:1, the volumetric flow rates of the fluid samples may be set to be substantially identical. In a first test, the flow rate of the fluid samples may be 0.1 microliters/second such that 100 seconds pass between when the fluid samples contact one another and when the mixed fluids pass through the filter and/or membrane. In a second test, the flow rate of the fluid samples may be 1.0 microliters/second such that 10 seconds pass between when the fluid samples contact one another and when the mixed fluids pass through the filter and/or membrane. In a third test, the flow rate of the fluid samples may be 10 microliters/second such that 1 second passes between when the fluid samples contact one another and when the mixed fluids pass through the filter and/or membrane. For each of the tests, the optical density of the fluid samples and the mixture after passing through the filter are measured. In some embodiments, the optical measurements may include optical density and/or fluorescence.

If the optical density values of the mixtures are substantially the same for each of the tests, the asphaltenes flocculated very quickly, which indicates that the commingled fluid is not very stable. However, if substantially more asphaltenes flocculated at the 100 second measurement than at the 1 second measurement, then the commingled fluid is slightly more stable.

While the above examples describe determining an optical density value of the fluid samples, a fluorescence value may alternatively or additionally be obtained.

FIG. 1 depicts an example wireline tool 151 that may be an environment in which aspects of the present disclosure may be implemented. The example wireline tool 151 is suspended in a wellbore 152 from the lower end of a multiconductor cable 154 that is spooled on a winch (not shown) at the Earth's surface. At the surface, the cable 154 is communicatively coupled to an electronics and processing system 156. The example wireline tool 151 includes an elongated body 158 that includes a formation tester 164 having a selectively extendable probe assembly 166 and a selectively extendable tool anchoring member 168 that are arranged on opposite sides of the elongated body 158. Additional components (e.g., 160) may also be included in the wireline tool 151.

The extendable probe assembly 166 may be configured to selectively seal off or isolate selected portions of the wall of the wellbore 152 to fluidly couple to an adjacent formation F and/or to draw fluid samples from the formation F. Accordingly, the extendable probe assembly 166 may be provided with a probe having an embedded plate. The formation fluid may be expelled through a port (not shown) or it may be sent to one or more fluid collecting chambers 176 and 178. The example wireline tool 151 also includes an example apparatus 180 that may be used to determine the compatibility of fluids (e.g., water), formation fluids obtained from different production zones and/or to determine an asphaltene content of formation fluid downhole, for example. As discussed in more detail below, the apparatus 180 may include one or more pumps, sample storage chambers (e.g., 176, 178), flowlines, sensors, mixers, filters, membranes, etc., that are used to determine fluid compatibility and/or if and/or an amount of asphaltenes that have flocculated from the fluid samples, once mixed. The amount of asphaltenes that flocculate from the mixed fluid samples is indicative of the compatibility and/or stability of crude oils from different production zones. The determined amount of asphaltenes that have flocculated from the mixed fluid samples may be none, some or a particular amount (e.g., a weight percent). In the illustrated example, the electronics and processing system 156 and/or a downhole control system are configured to control the extendable probe assembly 166, the apparatus 180 and/or the drawing of a fluid sample from the formation F.

Figure 2:
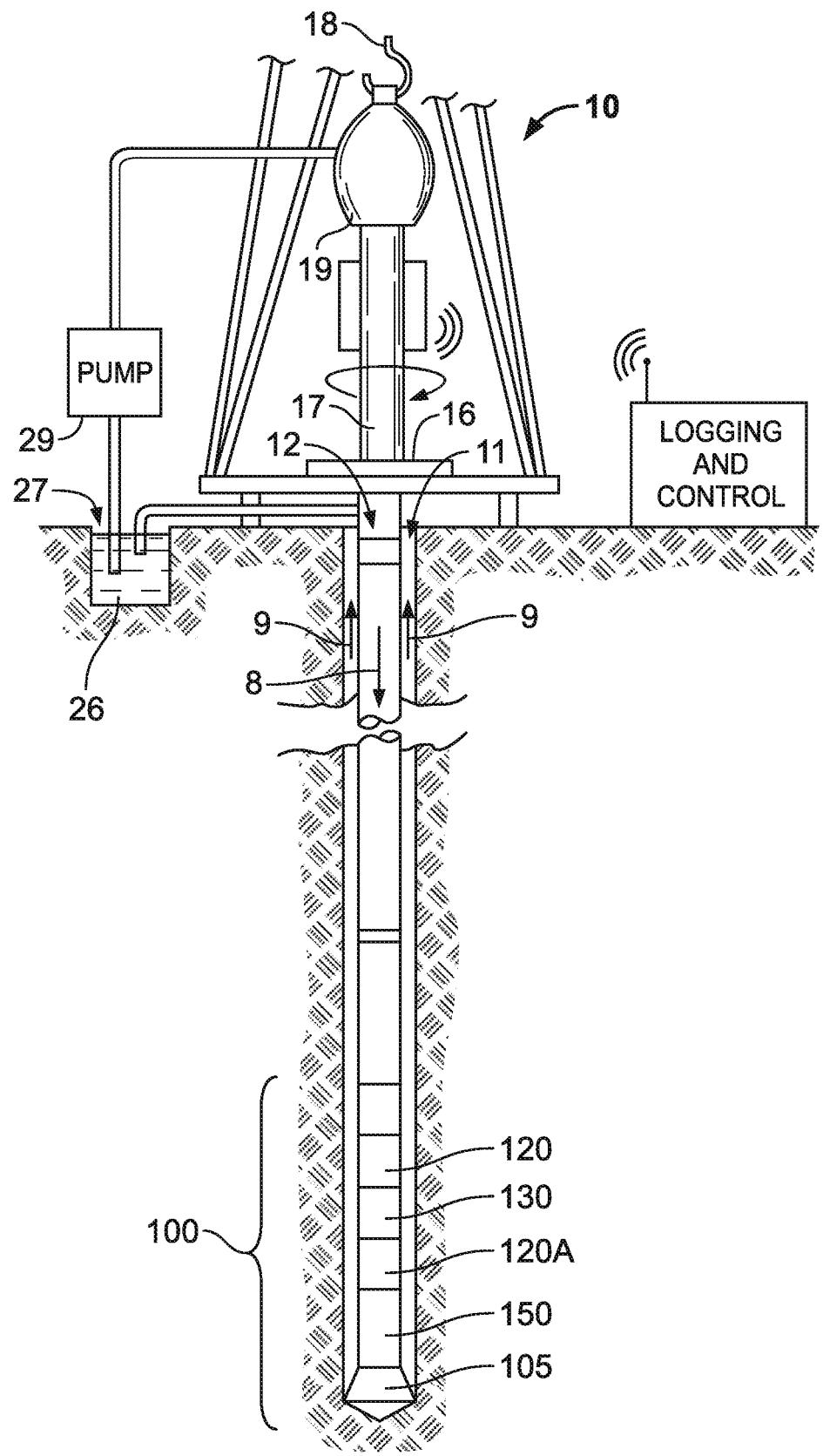
FIG. 2 illustrates another example system in which embodiments of the systems and methods for determining commingling compatibility of fluids from different formation zones can be implemented.

FIG. 2 illustrates a wellsite system in which the examples described herein can be employed. The wellsite can be onshore or offshore. In this example system, a borehole 11 is formed in subsurface formations by rotary drilling in a manner that is well known. However, the examples described herein can also use directional drilling, as will be described hereinafter.

A drill string 12 is suspended within the borehole 11 and has a bottom hole assembly 100 which includes a drill bit 105 at its lower end. The surface system includes a platform and derrick assembly 10 positioned over the borehole 11. The assembly 10 includes a rotary table 16, a kelly 17, a hook 18 and a rotary swivel 19. The drill string 12 is rotated by the rotary table 16 and energized by means not shown, which engages the kelly 17 at the upper end of the drill string 12. The drill string 12 is suspended from the hook 18, attached to a traveling block (also not shown), through the kelly 17 and the rotary swivel 19, which permits rotation of the drill string 12 relative to the hook 18. As is well known, a top drive system could alternatively be used.

In this example, the surface system further includes drilling fluid or mud 26 stored in a pit 27 formed at the well site. A pump 29 delivers the drilling fluid 26 to the interior of the drill string 12 via a port in the swivel 19, causing the drilling fluid 26 to flow downwardly through the drill string 12 as indicated by the directional arrow 8. The drilling fluid 26 exits the drill string 12 via ports in the drill bit 105, and then circulates upwardly through the annulus region between the outside of the drill string 12 and the wall of the borehole 11, as indicated by the directional arrows 9. In this manner, the drilling fluid 26 lubricates the drill bit 105 and carries formation cuttings up to the surface as it is returned to the pit 27 for recirculation.

The bottom hole assembly 100 includes a logging-while-drilling (LWD) module 120, a measuring-while-drilling (MWD) module 130, a roto-steerable system and motor 150, and the drill bit 105.

The LWD module 120 is housed in a special type of drill collar, as is known in the art, and can contain one or a plurality of known types of logging tools. It will also be understood that more than one LWD and/or MWD module can be employed, e.g., as represented at 120A. (References, throughout, to a module at the position of 120 can alternatively mean a module at the position of 120A as well.) The LWD module includes capabilities for measuring, processing and storing information, as well as for communicating with the surface equipment. In this example, the LWD module 120 includes a fluid sampling device.

The MWD module 130 is also housed in a special type of drill collar, as is known in the art, and can contain one or more devices for measuring characteristics of the drill string and drill bit. The MWD tool further includes an apparatus (not shown) for generating electrical power for the downhole system. This may include a mud turbine generator powered by the flow of the drilling fluid 26. However, other power and/or battery systems may be employed. In this example, the MWD module 130 includes one or more of the following types of measuring devices: a weight-on-bit measuring device, a torque measuring device, a vibration measuring device, a shock measuring device, a stick slip measuring device, a direction measuring device, and an inclination measuring device.

Figure 3:
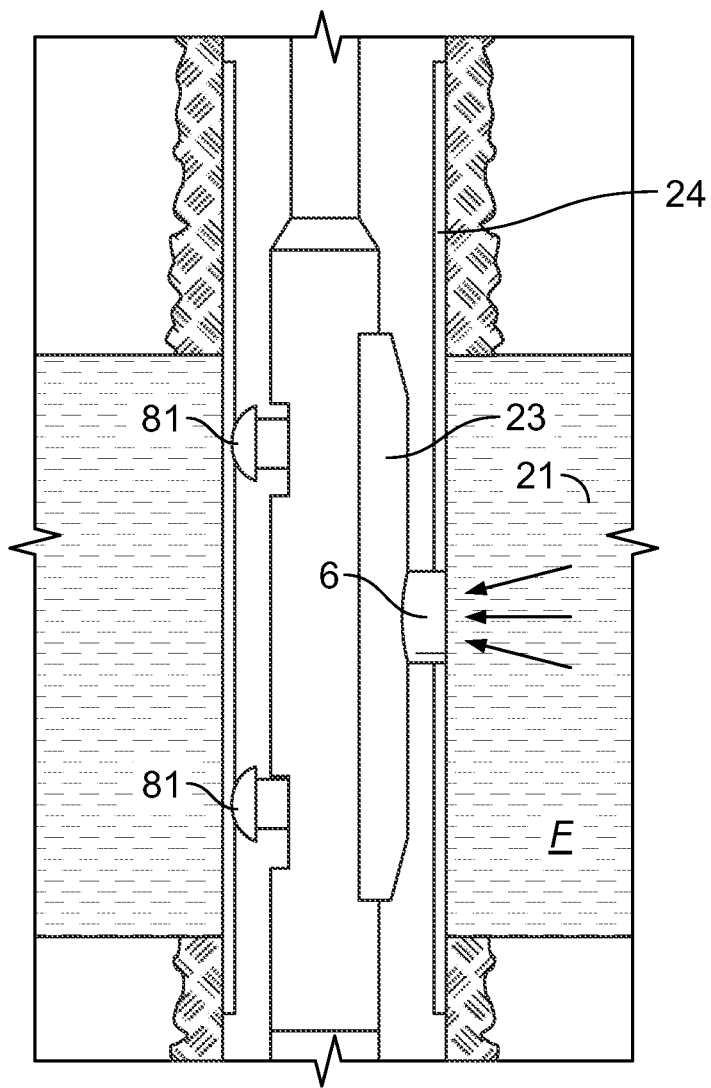
FIG. 3 illustrates another example system in which embodiments of the systems and methods for determining commingling compatibility of fluids from different formation zones can be implemented.

FIG. 3 is a simplified diagram of a sampling-while-drilling logging device of a type described in U.S. Pat. No. 7,114,562, incorporated herein by reference, utilized as the LWD module 120 or part of a LWD tool suite 120A. The LWD module 120 is provided with a probe 6 for establishing fluid communication with a formation F and drawing the fluid 21 into the tool, as indicated by the arrows. The probe 6 may be positioned in a stabilizer blade 23 of the LWD module 120 and extended therefrom to engage a borehole wall 24. The stabilizer blade 23 comprises one or more blades that are in contact with the borehole wall 24. Fluid drawn into the downhole tool using the probe 6 may be measured to determine, for example, pretest and/or pressure parameters. Additionally, the LWD module 120 may be provided with devices, such as sample chambers, for collecting fluid samples for retrieval at the surface. Backup pistons 81 may also be provided to assist in applying force to push the drilling tool and/or probe against the borehole wall 24.

Figure 4:
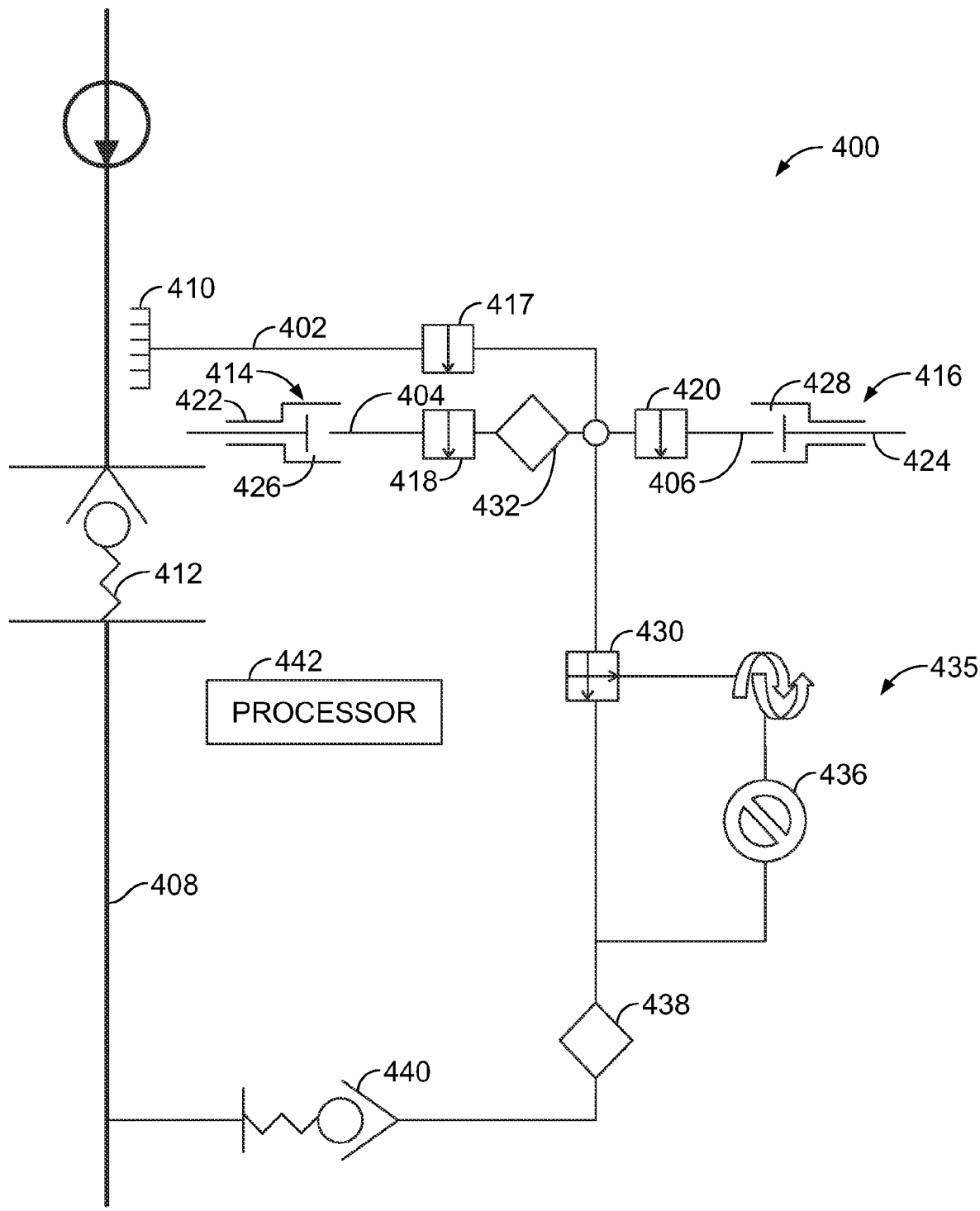
FIG. 4 illustrates various components of an example apparatus that can implement embodiments of the systems and methods for determining commingling compatibility of fluids from different formation zones.

FIG. 4 depicts an example apparatus 400 that may be used to determine the compatibility of formation fluids obtained from different production zones. The apparatus 400 includes first through third flowlines 402-406 that are fluidly coupled to a bypass flowline 408. To urge fluid to flow from the bypass flowline 408 through a membrane 410, the bypass flowline 408 includes an adjustable back pressure regulator 412 that enables an upstream pressure to be greater (e.g., 20 psi greater) than a downstream pressure. The membrane 410 is positioned adjacent the bypass flowline 408 and wicks particulate-free and/or water-free fluid from the bypass flowline 408 for downhole testing and/or analysis. This membrane 410 is an example of cross-flow filtration in some embodiments.

The apparatus 400 also includes a first sample storage chamber and pump 414 and a second sample storage chamber and pump 416. First, second and third fluid control devices (e.g., valves) 417, 418 and/or 420 control fluid flow relative to the respective storage chambers and pumps 414 and 416. In this example, the sample storage chambers and pumps 414 and 416 include pistons (e.g., motorized micropistons) 422, 424 and first and second chambers (e.g., piston bores) 426, 428. When the pistons 422, 422 retract, fluid can be pumped into and retained in the respective chambers 426, 428. However, any other configuration of pumps and/or storage chambers may be used instead.

Prior to obtaining and/or storing a first sample, fluid may be pumped through the first flowline 402 and analyzed and/or tested for quality and/or other parameters (e.g., optical density). Once it is determined to obtain the first sample, the apparatus 400 is positioned in the borehole adjacent a first formation zone and fluid is extracted from the first formation zone. The extracted fluid flows through the bypass flowline 408, the membrane 410 and the flowlines 402 and 404 to the first chamber 426. When obtaining the first sample, the first and second valves 417 and 418 are in the open position, the third valve 420 is in a closed position and a fourth valve 430 is in a position to direct fluid flow back to the bypass flowline 408. Once obtained, the first sample may be held in the first chamber 426 at a particular pressure (e.g., an overpressure, etc.).

Prior to obtaining and/or storing a second sample, fluid may be pumped through the first flowline 402 and analyzed and/or tested for quality and/or other parameters (e.g., optical density). Once it is determined to obtain the second sample, the apparatus 400 is positioned adjacent a second formation zone and fluid is extracted from the second formation zone. The extracted fluid flows through the bypass flowline 408, the membrane 410 and the flowlines 402 and 406 to the second chamber 428. When obtaining the second sample, the first and third valves 417, 420 are in the open position, the fourth valve 430 is in the position to direct fluid flow back to the bypass flowline 408 and the second valve 418 is in the closed position. Once obtained, the second sample may be held in the second chamber 428 at a particular pressure (e.g., an overpressure, etc.).

To determine a first value of a parameter for the first sample, with the first and third valves 417, 420 in the closed position and the fourth valve 430 directing fluid flow back to the bypass flowline 408, the second valve 418 is opened and the piston 422 pumps and/or urges a portion of the first sample from the first chamber 426 through the second flowline 404 and through and/or adjacent to a sensor 432. The sensor 432 then determines a first value of a parameter and/or optical density value for the first sample.

To determine a second value of the parameter for the second sample, with the first and second valves 417, 418 in the closed position and the fourth valve 430 directing fluid flow back to the bypass flowline 408, the third valve 420 is opened and the pump 424 pumps and/or urges a portion of the second sample from the second chamber 428 through the third flowline 406 and toward the sensor 432. The sensor 432 may be an optical density sensor that determines a second value of a parameter and/or optical density value for the second sample.

With the optical densities of the first and second samples obtained, the first valve 417 in the closed position and the fourth valve 430 directing fluid flow toward a mixer 435, the respective pistons 422 and 424 pump and/or urge a portion of the first and second samples from the chambers 426, 428 through the flowlines 404, 406 and/or 402 and toward the mixer 435. The pistons 422 and 424 may selectively and simultaneously pump the first and second samples at the same, similar or different flowrates. The mixer 435 may be an active and/or passive mixer including a torturous flowpath that accelerates the rate at which the samples mix. Mixing the samples may cause asphaltenes to flocculate from the mixture.

In this example, a filter 436 is positioned within the flowpath of the mixer 435. The filter 436 is configured to substantially prevent flocculated asphaltenes from flowing therethrough. After the mixed fluids have passed through the filter 436, the mixed fluid samples are directed through and/or adjacent to a second sensor 438, through a check valve 440 and back to the bypass flowline 408. The second sensor 438 may be an optical density sensor that determines a third value of a parameter and/or optical density value of the mixed samples.

To determine if and/or an amount of asphaltenes that may have flocculated when mixing the fluid samples, a processor 442 may average the first and second optical density values to generate an average optical density value. The processor 442 may then compare the average optical density value to the third optical density value. If the third optical density value is less and/or different than the average optical density value, asphaltenes have flocculated from the mixed fluid samples and, thus, the fluid samples may not be compatible. If the third optical density value is substantially similar to the average optical density value, substantially no asphaltenes have flocculated from the mixed fluid samples and, thus, the fluid samples may be compatible.

In other examples, the example apparatus 400 can be used to measure asphaltene content of one or more fluids. In such examples, the apparatus 400 may be deployed downhole with one of the chambers 426 or 428 empty and the other of the chambers 426 or 428 filled with, for example, heptane. The initially empty chamber 426 or 428 is used to store (e.g., temporarily store) a fluid sample, once obtained, from a formation zone.

The asphaltene content of the obtained fluid sample may be determined by measuring a first optical density value of the fluid sample using the sensor 432, mixing the fluid sample and the heptane (e.g., 40 parts heptane to 1 part fluid sample) using the mixer 435 and filtering the mixture using the filter 436. As discussed above, the filter 436 may remove any asphaltenes that may precipitate from the fluid sample. The sensor 438 may be used to measure a second optical density value of the mixture, which is compared to the first optical density by the processor 442. If the first and second optical density values are substantially the same, then substantially no asphaltenes precipitated from the fluid sample. However, if the second optical density value is less than the first optical density value, asphaltenes have precipitated from the fluid sample. To determine an amount of asphaltenes contained in the fluid sample, a difference between the first and second optical density values may be interpreted using methods described in U.S. patent application Ser. No. 12/790,927, filed May 31, 2010. Fluid samples from multiple formation zones may be tested until all of the heptane is used. Once the chamber 426 or 428 storing the heptane is empty (i.e., all of the heptane has been used), the chamber 426 or 428 may store fluid samples to be used in a commingling analysis as disclosed herein.

Figure 5:
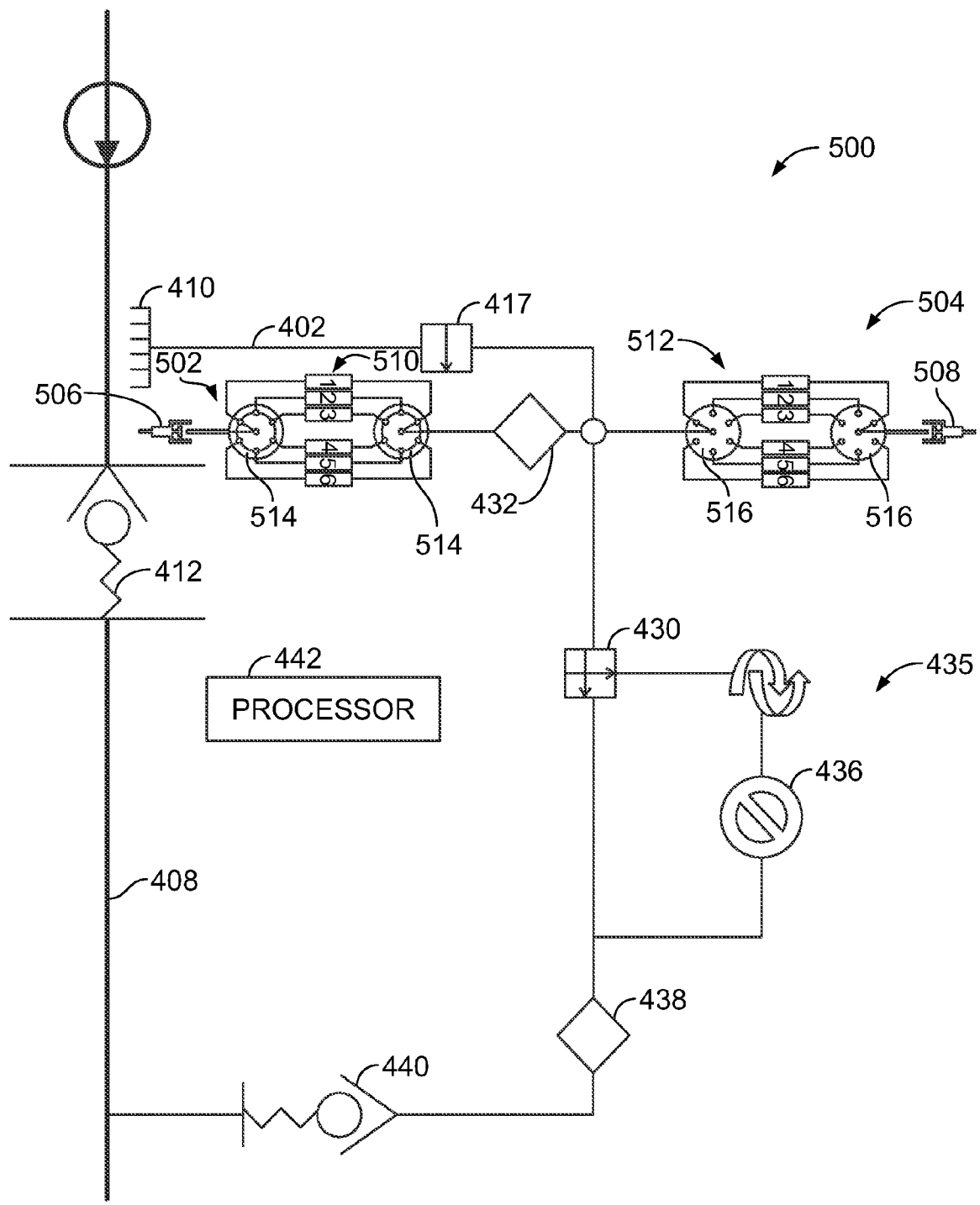
FIG. 5 illustrates another example apparatus that can implement embodiments of the systems and methods for determining commingling compatibility of fluids from different formation zones.

FIG. 5 depicts an example apparatus 500 that may be used to determine the compatibility of formation fluids obtained from different production zones. In contrast to the apparatus 400 of FIG. 4, the apparatus 500 includes example first storage chambers and a pump 502 and example second storage chambers and a pump 504. In this example, the sample storage chambers and pumps 502 and 504 include pistons (e.g., motorized micropistons) 506, 508 and a plurality of first and second chambers (e.g., piston bores) 510, 512. Each of the chambers 510 and 512 enables more than one fluid sample (e.g., formation fluid, formation water) to be obtained and/or stored and/or enables the storage of other fluids (e.g., toluene, heptane, water, gas, sea water, carbon dioxide, methane, ethane, propane or hydrogen sulfide or sulfur dioxide, etc.) that can be used downhole. Toluene may be used downhole to remove asphaltenes and/or other substances from the filter 436. Heptane may be mixed with a fluid sample to determine the asphaltene content thereof in a manner described in U.S. patent application Ser. No. 12/790,927, filed May 31, 2010, assigned to the assignee of the present patent and hereby incorporated herein by reference in its entirety.

In some examples, the example apparatus 500 may be used to determine the compatibility of water (e.g., dead or live waters). Water may be injected in the reservoir and/or mixed with different waters during enhanced oil recovery (EOR) processes. However, water to be injected and/or water to be mixed may be incompatible, which may lead to precipitation of scale. Using the examples disclosed herein, the compatibility of water may be determined using a process as described above. For example, if the compatibility of water from a first zone and a second zone is to be determined, the apparatus 500 may be used to obtain fluid samples from the respective zones. These samples can then be mixed using the mixer 435 and analyzed using the sensor 438 to identify any particulate (e.g., scale) that may have formed (e.g., the filter 436 may or may not be used). The observance of particulate may be identified by light scattering when shone through the fluid. If substantially no particulate is identified, the water from the first and second zones is substantially compatible. However, if the particulate is identified, the water from the first and second zones is not substantially compatible.

In some examples, one or more gasses (e.g., carbon dioxide, methane, ethane, propane or hydrogen sulfide or sulfur dioxide) may be injected into a reservoir to decrease the viscosity of the oil. However, depending on the temperature, pressure and oil/gas ratios, injecting such gasses may cause asphaltenes to precipitate. The precipitation of asphaltenes may negatively impact reservoir porosity by plugging formation pores and/or decreasing production rates.

In some example, the optical density of the oil, and the optical density of the oil and the gas mixture are measured using, for example, the sensors 432 and/or 438, in a manner as described above. The optical density values may be compared to determine whether the addition of gas caused asphaltene to flocculate. Based on the comparison, a concentration of gas (e.g., the gas/oil ratio) may be changed. If the addition of the gas to the fluid did not cause asphaltenes to flocculate, the optical density values are to be substantially the same. If the addition of the gas to the fluid caused asphaltenes to flocculate, the optical density value of the mixture is less than the optical density value of the fluid without the gas. In some examples to quantify an amount of asphaltenes that flocculated, in accordance with the teachings of this disclosure, the asphaltene content versus optical density method may be used.

To control fluid flow relative to the respective chambers 510, 512, the piston 506 can be selectively fluidly coupled to one of the first chambers 510 using a fluid control device(s) 514 and the piston 508 can be selectively fluidly coupled to one of the second chambers 512 using a fluid control device(s) 516.

Figure 6:
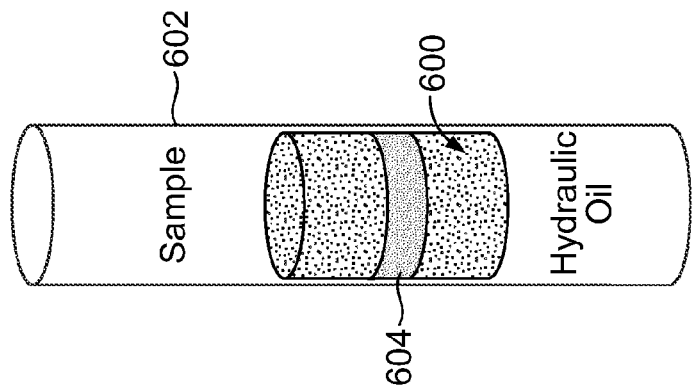
FIG. 6 illustrates an example apparatus that can implement embodiments of the systems and methods for determining commingling compatibility of fluids from different formation zones.

FIG. 6 depicts an example floating piston 600 positioned in a piston bore 602. The piston 600 includes an O-ring 604 to substantially separate hydraulic oil used to move the piston 600 from the sample obtained.

Figure 7:
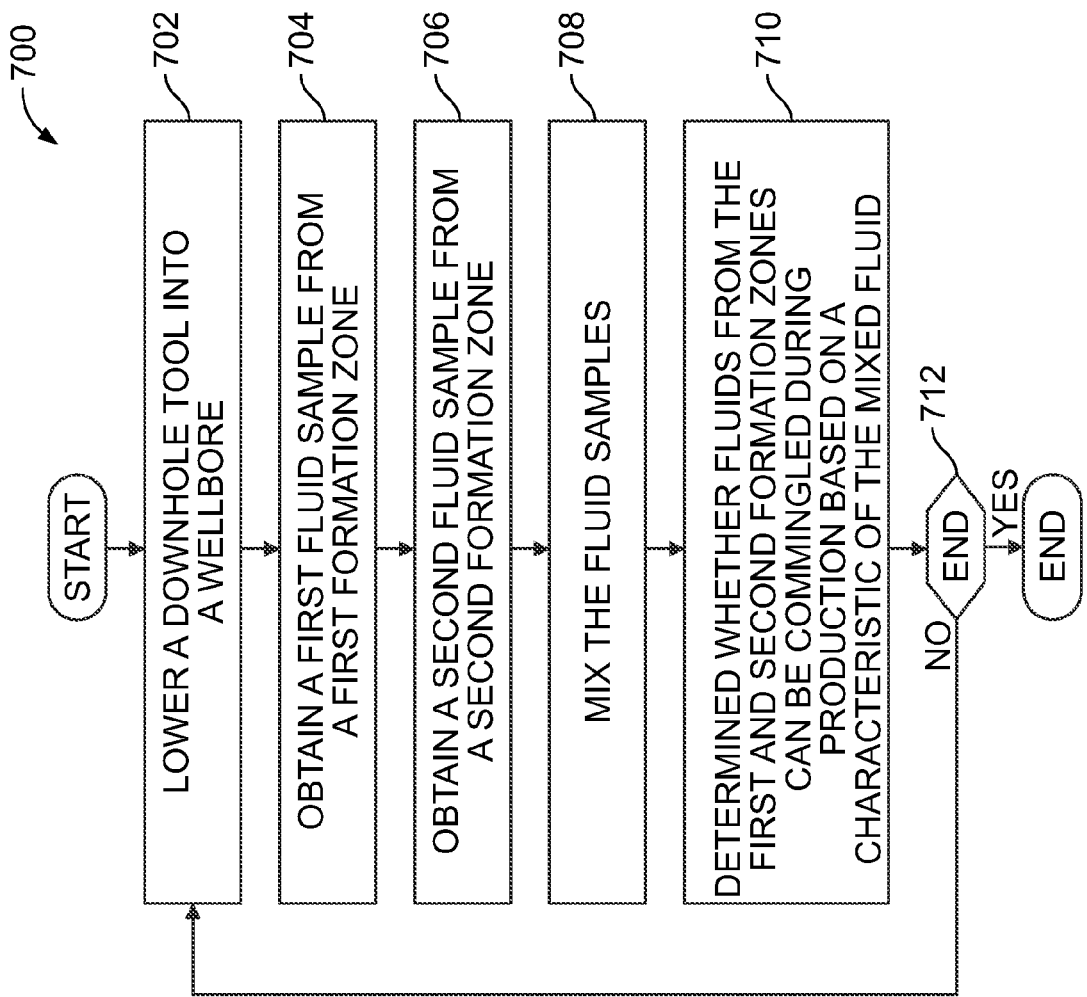
FIG. 7 illustrates an example method for determining commingling compatibility of fluids from different formation zones.

A flowchart representative of an example method that may be used to implement the apparatus 180, 400 and/or 500 of FIGS. 1, 4 and 5 and/or the examples disclosed herein is shown in FIG. 7. In this example, the method may be implemented using machine readable instructions comprising a program for execution by a processor such as the processor P105 shown in the example processor platform P100 discussed below in connection with FIG. 13 and/or the processor 442 of FIGS. 4 and/or 5. The program may be embodied in software stored on a tangible computer readable medium such as a CD-ROM, a floppy disk, a hard drive, a digital versatile disk (DVD), a BluRay disk, or a memory associated with the processor P105, but the entire program and/or parts thereof could alternatively be executed by a device other than the processor P105 and/or embodied in firmware or dedicated hardware. Further, although the example program is described with reference to the flowchart illustrated in FIG. 7, many other methods of implementing the example apparatus 180, 400 and/or 500 may alternatively be used. For example, the order of execution of the blocks may be changed, and/or some of the blocks described may be changed, eliminated or combined.

As mentioned above, the example operations of FIG. 7 may be implemented using coded instructions (e.g., computer readable instructions) stored on a tangible computer readable medium such as a hard disk drive, a flash memory, a read-only memory (ROM), a compact disk (CD), a digital versatile disk (DVD), a cache, a random-access memory (RAM) and/or any other storage media in which information is stored for any duration (e.g., for extended time periods, permanently, brief instances, for temporarily buffering, and/or for caching of the information). As used herein, the term tangible computer readable medium is expressly defined to include any type of computer readable storage and to exclude propagating signals. Additionally or alternatively, the example operations of FIG. 7 may be implemented using coded instructions (e.g., computer readable instructions) stored on a non-transitory computer readable medium such as a hard disk drive, a flash memory, a read-only memory, a compact disk, a digital versatile disk, a cache, a random-access memory and/or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals. As used herein, when the phrase "at least" is used as the transition term in a preamble of a claim, it is open-ended in the same manner as the term "comprising" is open ended. Thus, a claim using "at least" as the transition term in its preamble may include elements in addition to those expressly recited in the claim.

The example method 700 may be used to implement the examples described herein. While the below method 700 describes a commingling analysis, this method 700 may alternatively be used to determine the asphaltene content of a fluid sample obtained. In such examples, a downhole tools is lowered into a wellbore with one of the chambers 426, 428, 510 and/or 512 filled with heptane and the other of the chambers 426, 428, 510 and/or 512 to be filled with a fluid sample, once obtained. Prior to mixing the fluid sample and the heptane, an optical cell(s) may determine a first optical density value for a portion of the first sample. The fluid sample and the heptane are then pumped toward and/or through the mixer 435 having a torturous flowpath and/or the filter 436. A second optical density value of the filtered mixture may be determined. To determine an amount of asphaltenes contained in the fluid sample, a difference between the first and second optical density values may be interpreted using methods described in U.S. patent application Ser. No. 12/790,927, filed May 31, 2010.

Turning to method of FIG. 7, initially, a downhole tool such as the wireline tool 151 may be lowered into a wellbore (block 702). The wireline tool may then obtain a first sample from a first formation zone (block 704) and a second sample from a second formation zone (block 706). The first and second formation zones may be independent from one another. Using pumps 422, 424, 506 and/or 508, the samples may be pumped to and stored in respective chambers 426, 428, 510 and/or 512 at any suitable pressure.

Prior to mixing the samples, an optical cell(s) may independently determine a first optical density value for a portion of the first sample and a second optical density value for a portion of the second sample. The fluid samples may then be mixed and/or commingled by independently pumping the fluid samples from the respective sample chambers 426, 428, 510 and/or 512 at a controlled flow rate(s) (e.g., substantially equal volumetric flow rates, different flow rates) toward and/or through the mixer 435 having a torturous flowpath and/or the filter 436 (block 708).

It may then be determined whether the first and second formation zones can be commingled during production based on a characteristic of the mixed fluids (block 710). In some examples, the characteristic is associated with an amount of asphaltenes that have flocculated when mixing the fluid samples. The amount of flocculated asphaltenes can be determined by obtaining a third optical density value for the mixed fluid samples, averaging the first and second density values to generate an average value and then comparing the average value to the third optical density value. If the third optical density value is less than the average optical density value, asphaltenes have flocculated from the mixed fluid samples and have been filtered out of the mixed fluid samples by the filter 436. If the third optical density value is substantially similar to the average optical density value, substantially no asphaltenes have flocculated from the mixed fluid samples. In some examples, a difference between the third optical density and the average optical density corresponds to the optical spectrum of the asphaltenes in the samples. The asphaltene content of the fluid samples can be determined using a calibration curve, the optical density difference and/or a coefficient of determination ($R^2$).

While an example manner of implementing the examples disclosed herein has been illustrated in FIG. 7, one or more of the elements, processes and/or operations illustrated in FIG. 7 may be combined, divided, re-arranged, omitted, eliminated and/or implemented in any other way. Further, the example apparatus 180, 400 and/or 500 and/or, more generally, the example method 700 of FIG. 7 may be implemented by hardware, software, firmware and/or any combination of hardware, software and/or firmware. Thus, for example, any of the apparatus 180, 400 and/or 500 and/or, more generally, the example method could be implemented by one or more circuit(s), programmable processor(s), application specific integrated circuit(s) (ASIC(s)), programmable logic device(s) (PLD(s)) and/or field programmable logic device(s) (FPLD(s)), etc. When any of the apparatus or system claims of this patent are read to cover a purely software and/or firmware implementation, at least one of the example apparatus 180, 400 and/or 500 are hereby expressly defined to include a tangible computer readable medium such as a memory, DVD, CD, BluRay, etc., storing the software and/or firmware. Further still, the example method of FIG. 7 may include one or more elements, processes and/or operations in addition to, or instead of, those illustrated in FIG. 7, and/or may include more than one of any or all of the illustrated elements, processes and operations.

Figure 8:
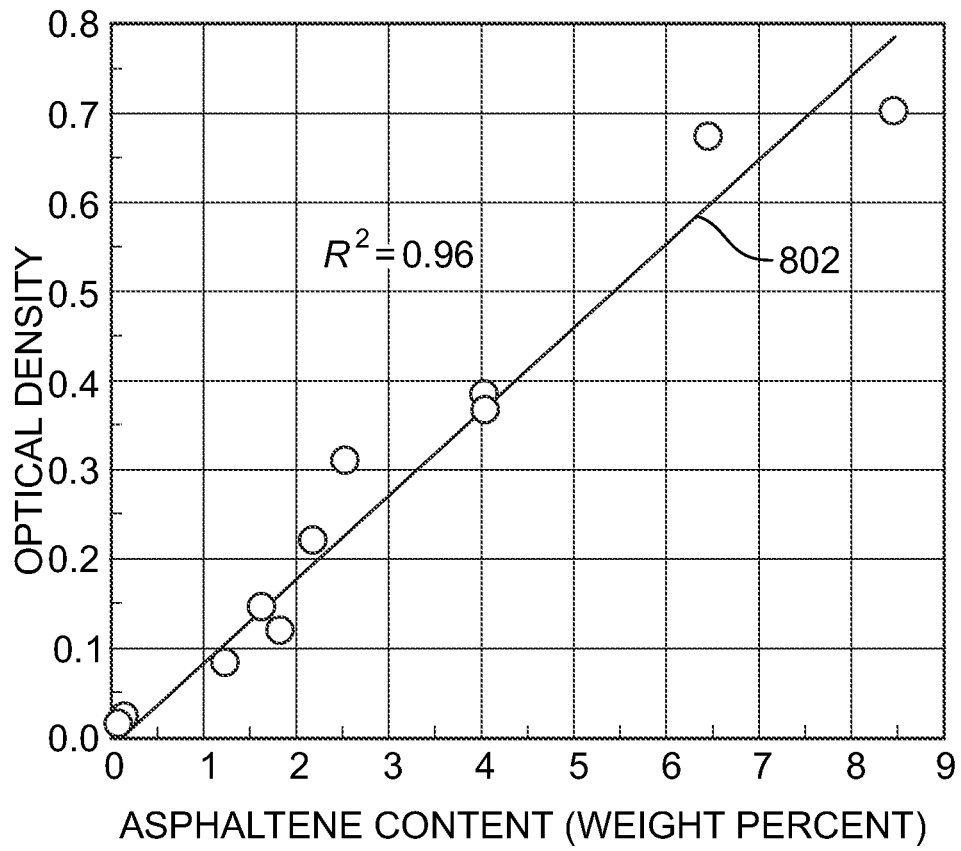
FIG. 8 is an example plot obtained using the examples disclosed herein.

FIG. 8 is an example plot of optical densities of various fluid samples in which the optical spectra of filtered mixed fluids (e.g., the first and second fluid samples) have been subtracted from the average optical spectra of the fluid samples. FIG. 8 depicts optical density at a particular wavelength (i.e., 600 nm) for asphaltenes of different fluid samples and/or crude oil samples. Reference number 802 represents a linear model generated using the resulting optical density and asphaltene contents of the samples. In this example, the coefficient of determination is 0.96.

Figure 9:
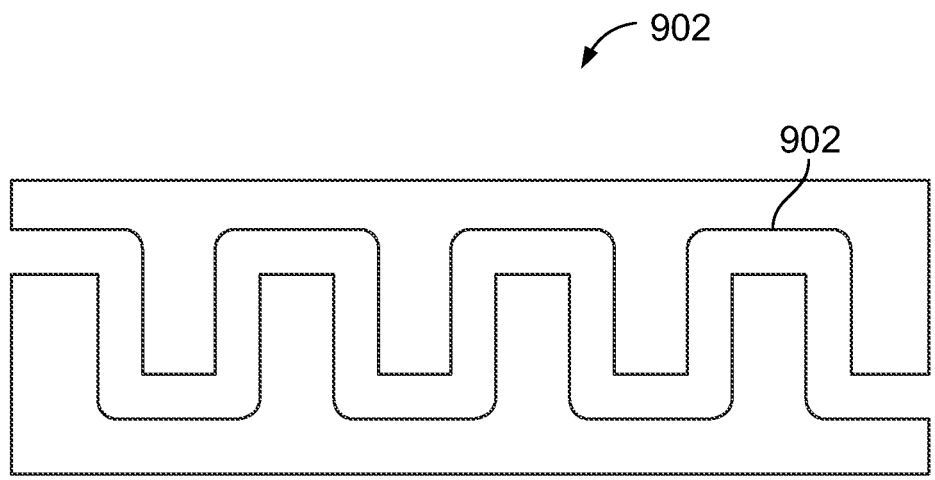
FIG. 9 illustrates an example mixer that can be used to implement the examples described herein.

FIG. 9 depicts an example mixer 900 that can be used to implement the examples described herein. The example mixer 900 includes a flowpath 902 that is torturous and/or has a plurality of bends and/or curves.

Figure 10:
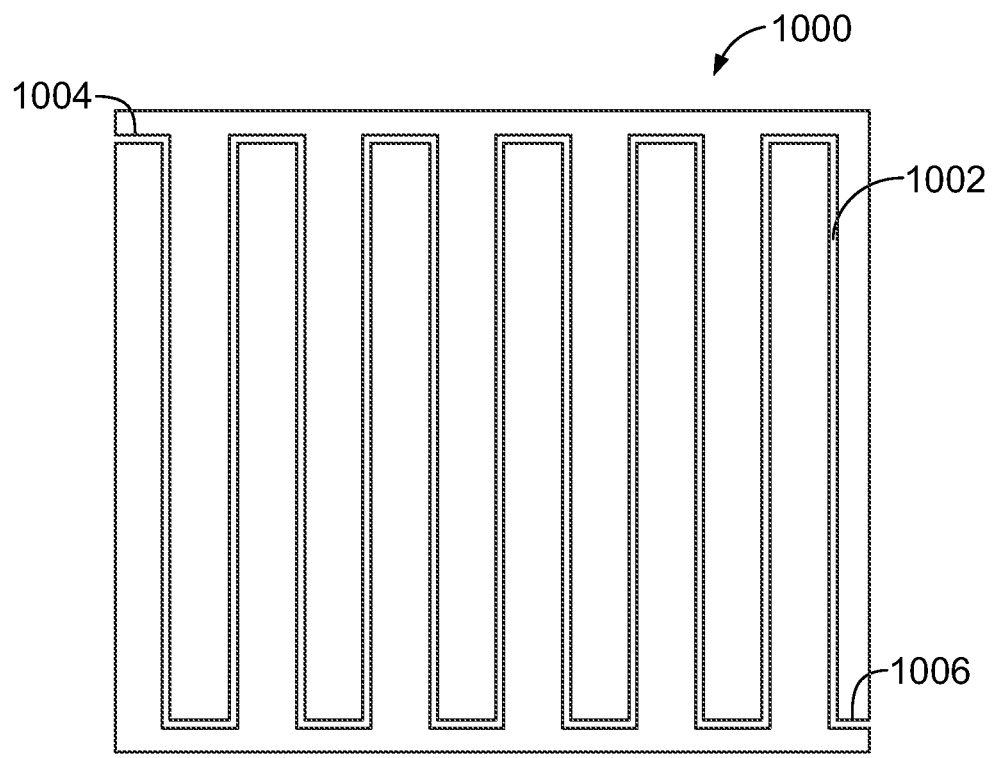
FIGS. 10 and 11 illustrate an example filter that can be used to implement the examples described herein.
Figure 11:
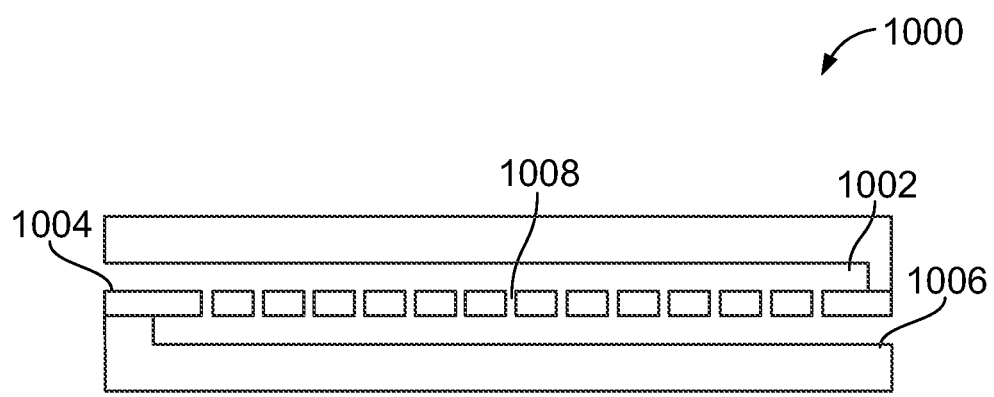

FIGS. 10 and 11 depict an example filter 1000 that can be used to implement the examples described herein. Specifically, FIG. 10 depicts a top view of the example filter 1000 and FIG. 11 depicts a side view of the example filter 1000. The example filter 1000 includes a flowpath 1002 having an inlet 1004, an outlet 1006 and a membrane 1008. The fluid path 1002 may be relatively long to enable the fluid sample(s) to be in contact with membrane 1008. The membrane 1008 defines pores (e.g., relatively small pores) 1010 that block the passage of flocculates (e.g., large flocculates) but enables the passage of the fluid sample(s) therethrough.

Figure 12:
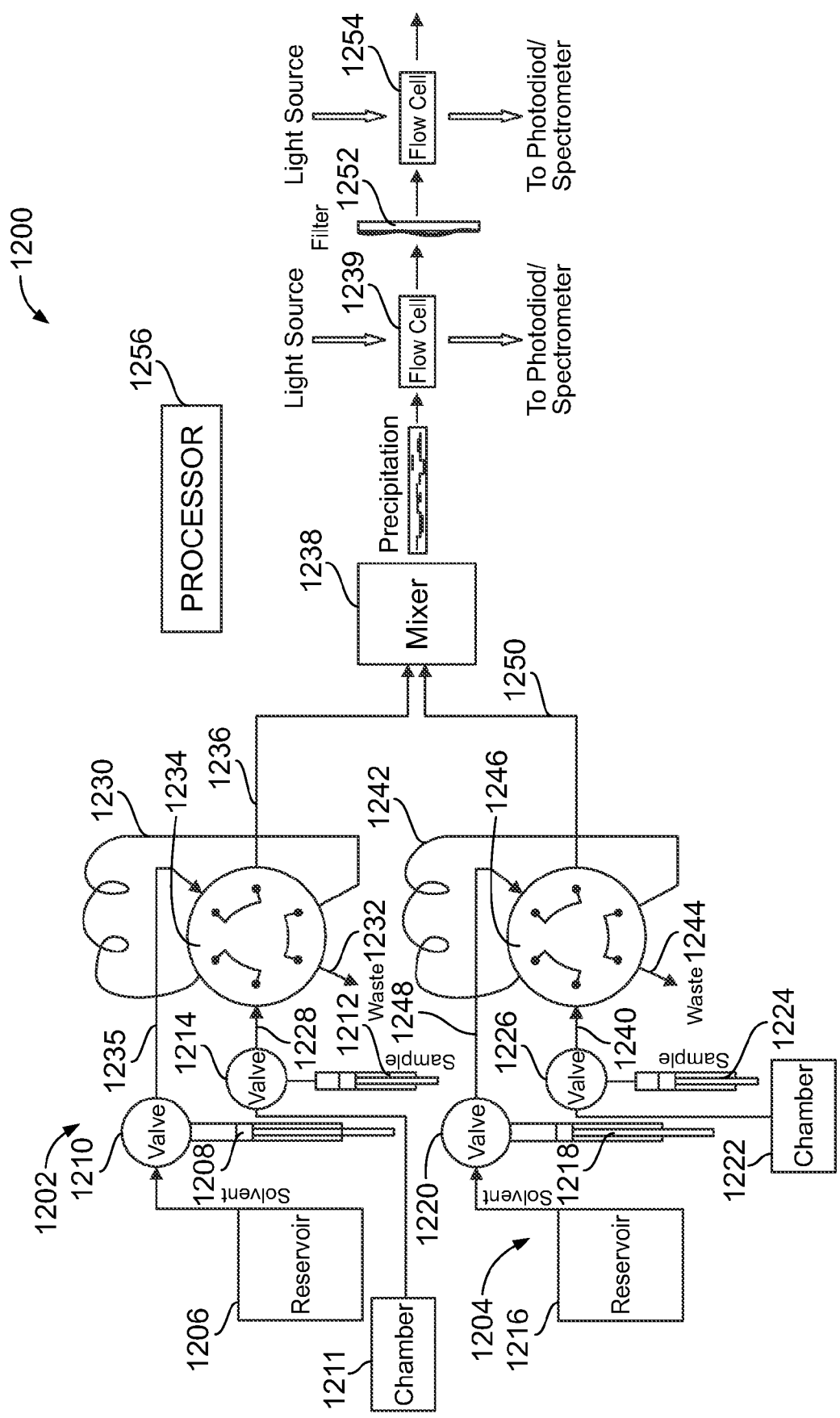
FIG. 12 illustrates various components of an example apparatus that can implement embodiments of the systems and methods for determining commingling compatibility of fluids from different formation zones.

FIG. 12 depicts an example apparatus 1200 that may be used to determine the compatibility of formation fluids obtained from different production zones. The apparatus 1200 includes first and second solvent and fluid sample assemblies 1202 and 1204. The first solvent and fluid sample assembly 1202 includes a solvent chamber 1206 that is selectively fluidly coupled to a first pump 1208 via a first valve 1210. The first solvent and fluid sample assembly 1202 also includes a fluid sample chamber 1211 that is selectively fluidly coupled to a second pump 1212 via a second valve 1214. The second solvent and fluid sample assembly 1204 includes a solvent chamber 1216 that is selectively fluidly coupled to a third pump 1218 via a third valve 1220. The second solvent and fluid sample assembly 1204 also includes a fluid sample chamber 1222 that is selectively fluidly coupled to a fourth pump 1224 via a fourth valve 1226.

In operation, to determine a first optical density value of a first sample, the first valve 1210 is operated to enable the first pump 1208 to be filled with solvent from the reservoir 1206 and the second valve 1214 is operated to enable the second pump 1212 to be filled with sample fluid from the chamber 1211. The chamber 1211 may be filled with fluid (e.g., formation fluid, water, gas, etc.) downhole or uphole. To ensure that flowlines 1228 and 1230 are filled with the first fluid sample (e.g., primed with formation fluid), the second valve 1214 is operated to enable the second pump 1212 to pump the fluid sample through the flowlines 1228 and 1230 and to waste (e.g., to the borehole) 1232. A valve (e.g., a six way valve) 1234 may then be rotated (e.g., counterclockwise) to enable a flowline 1235 to be fluidly coupled to the flowline 1230, a flowline 1236 and a mixer 1238. Thus, pumping the solvent through the flowlines 1235, 1230, 1236 via the pump 1208 pushes the fluid sample from the flowline 1230 to the mixer 1238 while also removing any asphaltenes that may flocculate. After the first sample passes through the mixer 1238, a sensor 1239 may determine a first optical density value of the first sample.

Similarly, to determine a second optical density value of the second sample, the third valve 1220 is operated to enable the third pump 1218 to be filled with solvent from the reservoir 1216 and the third valve 1226 is operated to enable the second pump 1224 to be filled with sample fluid from the chamber 1222. To ensure that flowlines 1240 and 1242 are filled with the second fluid sample (e.g., primed with formation fluid), the fourth valve 1226 is operated to enable the fourth pump 1224 to pump the fluid sample through the flowlines 1240 and 1242 and to waste (e.g., to the borehole) 1244. A valve (e.g., a six way valve) 1246 may then be rotated (e.g., counterclockwise) to enable a flowline 1248 to be fluidly coupled to the flowline 1242, a flowline 1250 and the mixer 1238. Thus, pumping the solvent through the flowlines 1248, 1242, 1250 via the pump 1218 pushes the fluid sample from the flowline 1242 to the mixer 1238 while also removing any asphaltenes that may flocculate. After the second sample passes through the mixer 1238, the sensor 1240 may determine a second optical density value of the second sample.

With the optical density values of the first and second samples obtained and the flowlines 1230 and 1242 filled with fluid samples, the respective pumps 1208, 1218 pump and/or urge the first and second fluid samples from the flowlines 1230 and 1242 toward the mixer 1238. The pumps 1208 and/or 1218 may selectively and simultaneously pump the first and second fluid samples at the same, similar or different flowrates. The mixer 1238 may be an active and/or passive mixer including a torturous flowpath that accelerates the rate at which the samples mix. Mixing the samples may cause asphaltenes to flocculate from the mixture.

In this example, the mixed fluid samples pass through a filter 1252 that substantially prevents flocculated asphaltenes from flowing therethrough. After the mixed fluids have passed through the filter 1252, the mixed fluids pass by a sensor 1254 that determines a third optical density value of the mixed fluids.

To determine if and/or an amount of asphaltenes that may have flocculated when mixing the fluid samples, a processor 1256 may average the first and second optical density values to generate an averaged optical density value. The processor 1256 may then compare the averaged optical density value to the third optical density value. If the third optical density value is less and/or different than the averaged optical density value, asphaltenes have flocculated from the mixed fluid samples and, thus, the fluid samples may not be compatible. If the third optical density value is substantially similar to the averaged optical density value, substantially no asphaltenes have flocculated from the mixed fluid samples and, thus, the fluid samples may be compatible.

Figure 13:
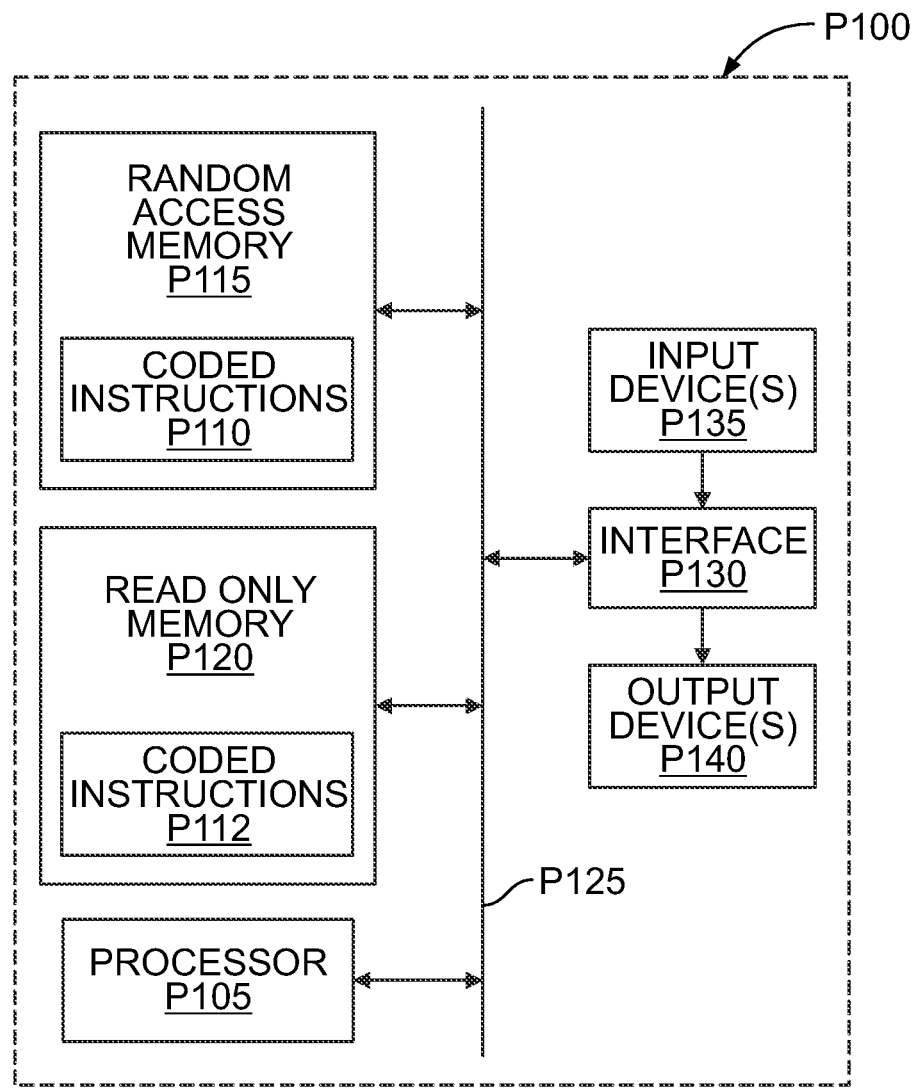
FIG. 13 is a schematic illustration of an example processor platform that may be used and/or programmed to implement any or all of the example systems and methods disclosed herein.

FIG. 13 is a schematic diagram of an example processor platform P100 that may be used and/or programmed to implement to implement the electronics and processing system 156, the processor 442 and/or any of the examples described herein. For example, the processor platform P100 can be implemented by one or more general purpose processors, processor cores, microcontrollers, etc.

The processor platform P100 of the example of FIG. 13 includes at least one general purpose programmable processor P105. The processor P105 executes coded instructions P110 and/or P112 present in main memory of the processor P105 (e.g., within a RAM P115 and/or a ROM P120). The processor P105 may be any type of processing unit, such as a processor core, a processor and/or a microcontroller. The processor P105 may execute, among other things, the example methods and apparatus described herein.

The processor P105 is in communication with the main memory (including a ROM P120 and/or the RAM P115) via a bus P125. The RAM P115 may be implemented by dynamic random-access memory (DRAM), synchronous dynamic random-access memory (SDRAM), and/or any other type of RAM device, and ROM may be implemented by flash memory and/or any other desired type of memory device. Access to the memory P115 and the memory P120 may be controlled by a memory controller (not shown).

The processor platform P100 also includes an interface circuit P130. The interface circuit P130 may be implemented by any type of interface standard, such as an external memory interface, serial port, general purpose input/output, etc. One or more input devices P135 and one or more output devices P140 are connected to the interface circuit P130.

The examples disclosed herein can be used to determine the compatibility of two or more fluids (e.g., formation fluids, waters, gas and water, etc.) and/or to determine an asphaltene content of a formation fluid (e.g., crude oil) downhole. In some examples, two formation fluids are mixed at different ratios to determine their compatibility at the ratio at which the fluids are to be mixed during production (e.g., 30% of fluid from a first formation zone and 70% from a second formation zone).

The examples disclosed herein can be used to determine compatibility of mixing two or more fluids by varying an amount of time that the fluids are in contact with one another (e.g., varying the flow rate) prior to determining an amount of asphaltene precipitation. For example, if a long period (e.g., 100 seconds) of time lapses prior to analysis and it is determined that no asphaltenes have precipitated from the mixed fluids, the mixed fluids are relatively stable. If a short period (e.g., one second) of time lapses prior to analysis and it is determined that asphaltenes have precipitated from the mixed fluids, the mixed fluids are not relatively stable.

In other examples an apparatus in accordance with the teachings of this disclosure includes a plurality of chambers and/or bottles (e.g., two, six) that may be used to independently house, obtain, dispense, fluid samples, solvents, gasses, etc. The apparatus may include one or more valves to direct the flow of fluid, solvent, gas, etc., to different flowlines and/or to different portions of the apparatus (e.g., the mixer, to the borehole, etc.). In some examples, a piston or other device is used to urge the fluid sample to flow toward the mixer. In other examples, a solvent or other substance (e.g., liquid, gas) is used to urge the fluid sample to flow toward the mixer. By mixing heptane with formation fluid, the examples disclosed herein can be used to determine an asphaltene content of the formation fluid downhole.

In some examples, before determining whether two formation fluids can be commingled without asphaltene flocculation, a determination can be made as to whether asphaltenes are present in fluid obtained from a first zone by measuring the asphaltene content of a fluid sample obtained therefrom. Similarly, a determination can be made as to whether asphaltenes are present in fluid obtained from a second zone by measuring the asphaltene content of a fluid sample obtained therefrom. In some examples, if the first and second formation zones are to be simultaneously produced and/or if asphaltenes are present in fluid from either of the formation zones, the compatibility of the fluid from the first and second zones may be determined by commingling the fluids and performing an analysis thereon.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words 'means for' together with an associated function.

The Abstract at the end of this disclosure is provided to comply with 37 C.F.R. §1.72(b) to allow the reader to quickly ascertain the nature of the technical disclosure. It is submitted with the understanding that it will not be used to interpret or limit the scope or meaning of the claims.

What is claimed is:

1. A method, comprising:
   filtering a first fluid via a first filter;
   optically measuring the first fluid;
   combining a second fluid with the first fluid after optically measuring the first fluid;
   filtering the combined first and second fluids via a second filter to remove precipitates;
   optically measuring the combined first and second fluids after the filtering of the combined first and second fluids; and
   using the optical measurement of the first fluid and the optical measurement of the combined first and second fluids to determine (a) whether or not precipitate was removed from the combined first and second fluids by the second filter or (b) an amount of precipitate removed from the combined first and second fluids by the second filter,
   wherein the first fluid comprises material from a subterranean formation, and
   wherein the first fluid is a formation fluid from a first zone of the formation and the second fluid is a formation fluid from a second zone of the formation.

2. The method of claim 1, wherein the formation comprises a wellbore.

3. The method of claim 1, wherein the second fluid promotes precipitation upon its exposure to asphaltene.

4. The method of claim 1, wherein the combining comprises use of a pump.

5. The method of claim 1, further comprising storing a sample of the first fluid.

6. The method of claim 1, wherein the combining the first and second fluids includes combining the first and second fluids in a ratio corresponding to a ratio between an expected production rate of the first fluid from the first production zone and an expected production rate of the second fluid from the second production zone.

7. The method of claim 1, further comprising comparing the optical measurements of the first fluid and the combined first and second fluids.

8. The method of claim 1, further comprising optically measuring the second fluid prior to combining the first and second fluids.

9. The method of claim 7, further comprising estimating the first fluid's likelihood of forming precipitates with other fluids.

10. The method of claim 7, further comprising estimating the first fluid's asphaltene content.

11. The method of claim 8, further comprising determining, based on the optical measurement of the first fluid and the optical measurement of the second fluid, an average optical density of the first and second fluids before the first and second fluids are combined.

12. The method of claim 11, further comprising:
    determining, based on the optical measurement of the combined first and second fluids, an optical density of the combined first and second fluids after being filtered via the second filter.

13. The method of claim 12, wherein the determination of at least one of (a) whether or not precipitate was removed from the combined first and second fluids by the second filter and (b) an amount of precipitate removed from the combined first and second fluids by the second filter, is based on a comparison of (a) the determined average optical density of the first and second fluids before combination of the first and second fluids and (b) the determined density of the combined first and second fluids after being filtered via the second filter.

14. A method, comprising:
filtering a first fluid via a first filter, wherein the first fluid comprises material from a subterranean formation;
optically measuring the first fluid;
combining a second fluid with the first fluid after optically measuring the first fluid;
filtering the combined first and second fluids via a second filter to remove precipitates;
optically measuring the combined first and second fluids after the filtering of the combined first and second fluids;
using the optical measurement of the first fluid and the optical measurement of the combined first and second fluids to determine (a) whether or not precipitate was removed from the combined first and second fluids by the second filter or (b) an amount of precipitate removed from the combined first and second fluids by the second filter; and
repeating the filtering, optically measuring, combining, filtering, and optically measuring for a third fluid, wherein the third fluid is collected from an additional region of the subterranean formation.

15. The method of claim 14, further comprising estimating fluid compatibility of the first and third fluids.

16. The method of claim 15, wherein the fluid compatibility comprises the first fluid's likelihood of forming precipitates.

17. A method, comprising:
filtering a first fluid via a first filter;
optically measuring the first fluid;
combining a second fluid with the first fluid after optically measuring the first fluid;
filtering the combined first and second fluids via a second filter to remove precipitates;
optically measuring the combined first and second fluids after the filtering of the combined first and second fluids; and
using the optical measurement of the first fluid and the optical measurement of the combined first and second fluids to determine (a) whether or not precipitate was removed from the combined first and second fluids by the second filter or (b) an amount of precipitate removed from the combined first and second fluids by the second filter,
wherein the first fluid comprises material from a subterranean formation, and wherein the second fluid is selected to remove precipitates from a surface of the second filter.

18. The method of claim 17, wherein the second fluid is selected from the group consisting of toluene, heptane, pentane, octane, carbon dioxide, methane, ethane, propane, hydrogen sulfide, or sulfur dioxide.

* * * * *